(12) United States Patent
Kuyava

(10) Patent No.: US 7,407,482 B2
(45) Date of Patent: Aug. 5, 2008

(54) PENILE PROSTHESIS DEVICES AND METHODS

(75) Inventor: Charles C. Kuyava, Eden Prairie, MN (US)

(73) Assignee: AMS Research Corporation, Minnetonka, MN (US)

(*) Notice: Subject to any disclaimer, the term of this patent is extended or adjusted under 35 U.S.C. 154(b) by 323 days.

(21) Appl. No.: 10/956,713

(22) Filed: Oct. 1, 2004

(65) Prior Publication Data

US 2005/0075534 A1    Apr. 7, 2005

Related U.S. Application Data

(60) Provisional application No. 60/507,973, filed on Oct. 2, 2003.

(51) Int. Cl.
*A61F 2/00* (2006.01)
*A61F 5/00* (2006.01)

(52) U.S. Cl. .......................... 600/40; 606/148

(58) Field of Classification Search ............ 600/38–41; 606/148, 222–228; 206/438
See application file for complete search history.

(56) References Cited

U.S. PATENT DOCUMENTS

| | | | |
|---|---|---|---|
| 988,120 A | 3/1911 | Lott | |
| 1,863,057 A | 6/1932 | Innes | |
| 3,312,215 A | 4/1967 | Silber | |
| 3,344,791 A | 10/1967 | Foderick | |
| 3,397,699 A | 8/1968 | Kohl | |
| 3,797,478 A | 3/1974 | Walsh et al. | |
| 3,877,570 A * | 4/1975 | Barry | 206/63.3 |
| 3,954,102 A | 5/1976 | Buuck | |
| RE29,678 E * | 6/1978 | Antonini et al. | 206/571 |
| 4,222,377 A | 9/1980 | Burton | |
| 4,244,370 A | 1/1981 | Furlow et al. | |
| 4,267,829 A | 5/1981 | Burton et al. | |
| 4,383,525 A | 5/1983 | Scott et al. | |
| 4,407,278 A | 10/1983 | Burton et al. | |
| 4,489,732 A | 12/1984 | Hasson | |
| 4,537,183 A | 8/1985 | Fogarty | |
| 4,559,931 A * | 12/1985 | Fischell | 600/40 |
| 4,566,446 A | 1/1986 | Fogarty | |
| 4,571,241 A | 2/1986 | Christopher | |
| 4,590,927 A | 5/1986 | Porter et al. | |

(Continued)

OTHER PUBLICATIONS

Mulcahy, John J., "Distal Corporoplasty for Lateral Extrusion of Penile Prosthesis Cylinders," *The Journal of Urology*, vol. 161, pp. 193-195 (Jan. 1999).

(Continued)

*Primary Examiner*—John P Lacyk
(74) *Attorney, Agent, or Firm*—Jose' W. Jimenez; Kimberly K. Baxter; Gregory L. Koeller

(57) ABSTRACT

Penile implant devices and methods are disclosed. A penile implant device in accordance with the present invention includes an implantable penile prosthesis pre-connected to a needle by a suture. The needle and suture may also be at least partially enclosed in a sheath or the like. In accordance with the present invention, a penile prosthesis is connected to a needle by a suture during a pre-operative storage period of the penile implant device. For example, the penile prosthesis may be connected to the needle during manufacture of the penile implant device.

16 Claims, 14 Drawing Sheets

U.S. PATENT DOCUMENTS

| | | |
|---|---|---|
| 4,671,261 A | 6/1987 | Fischell |
| 4,710,169 A | 12/1987 | Christopher |
| 4,718,410 A | 1/1988 | Hakky |
| 4,782,826 A | 11/1988 | Fogarty |
| 5,048,510 A | 9/1991 | Hauschild et al. |
| 5,062,417 A | 11/1991 | Cowen |
| 5,063,914 A | 11/1991 | Cowen |
| 5,112,295 A | 5/1992 | Zinner et al. |
| 5,171,272 A | 12/1992 | Levius |
| 5,236,443 A | 8/1993 | Sontag |
| 5,250,020 A * | 10/1993 | Bley ............................ 600/40 |
| 5,295,965 A * | 3/1994 | Wilmot ...................... 604/136 |
| 5,344,388 A | 9/1994 | Maxwell et al. |
| 5,433,728 A | 7/1995 | Kim |
| 5,484,450 A | 1/1996 | Mohamed |
| 5,676,675 A | 10/1997 | Grice |
| 5,683,416 A | 11/1997 | McGregor et al. |
| 5,693,071 A | 12/1997 | Gorecki et al. |
| 5,693,072 A | 12/1997 | McIntosh |
| 5,704,895 A | 1/1998 | Scott et al. |
| 5,868,729 A | 2/1999 | Pelfrey |
| 5,891,164 A | 4/1999 | Dabir et al. |
| 5,895,424 A | 4/1999 | Steele, Sr. et al. |
| 5,897,572 A | 4/1999 | Schulsinger et al. |
| 5,902,320 A | 5/1999 | Matsutani et al. |
| 5,913,875 A | 6/1999 | Smith et al. |
| 5,993,408 A | 11/1999 | Zaleski |
| 6,129,741 A | 10/2000 | Wurster et al. |
| 6,159,233 A | 12/2000 | Matsuzawa |
| 6,171,233 B1 | 1/2001 | Willard |
| 6,322,581 B1 | 11/2001 | Fukuda et al. |
| 6,514,263 B1 | 2/2003 | Stefanchik et al. |
| 6,592,556 B1 * | 7/2003 | Thorne ....................... 604/192 |
| 6,723,042 B2 | 4/2004 | Almli et al. |
| 2004/0167574 A1 * | 8/2004 | Kuyava et al. .............. 606/224 |

OTHER PUBLICATIONS

Teleflex Medical brochure, "Experience the Force Fiber Advantage," Catalog No. 25-8208 (May 2004).

American Medical Systems, "AMS 700™ Penile Prosthesis," Operating Room Manual (2003).

* cited by examiner

PENILE PROSTHESIS DEVICES AND METHODS

CROSS REFERENCE TO RELATED APPLICATION

This application claims the benefit of U.S. Provisional Application Ser. No. 60/507,973, filed Oct. 2, 2003, entitled "PENILE PROSTHESIS DEVICES AND METHODS," which application is incorporated herein by reference in its entirety.

TECHNICAL FIELD

The present invention relates generally to medical devices and methods of using such devices in implant surgery. More particularly, the present invention relates to implantable penile prostheses and methods of making and implanting such prostheses.

BACKGROUND

One common treatment for impotence includes the use of a penile implant device. The penile implant device normally includes a pair of cylindrical prostheses that are implanted into the corpus cavernosae of the penis. In some instances, the prostheses are inflatable and are connected to a fluid-filled reservoir with a pump and valve assembly. In one configuration, for example, the pump assembly is implanted into the scrotum of the patient, and the reservoir is implanted in the abdomen. During use, the patient actuates the pump and fluid is transferred from the reservoir through the pump and into the prosthesis. This results in the inflation of the prosthesis and produces rigidity for a normal erection. When the patient desires to deflate the prosthesis, a valve assembly within the pump is actuated in a manner such that the fluid in the prosthesis is released back into the reservoir. This deflation returns the penis to a flaccid state.

Such penile implant devices require a delicate implant surgery to install. To reach a corpus cavernosa and implant a prosthesis, the surgeon first makes an incision at the base of the penis, such as where it meets the scrotum. The patient is prepared for the prosthesis after the surgeon has dilated each corpus cavernosa to create space for the prosthesis.

Once the patient has been prepared, the surgeon prepares an assembly that includes a cylindrical prosthesis and an inserter device known as a Furlow insertion tool. The Furlow insertion tool is well known in the art of such penile implants and is often used for this type of procedure. A Furlow insertion tool is a long slender device having a hollow barrel that contains a plunger device known as an obturator. The Furlow insertion tool can be used to insert a needle known as a Keith needle, into the corpus cavernosa, and through the glans of the penis. The Keith needle is also a well-known tool used in many areas of medicine that looks much like a heavy sewing needle and is used to pierce tissue. The Keith needle fits within the barrel of the Furlow insertion tool and is ejected from the forward end by using the obturator.

Prior to installing each prosthesis of a penile implant device, a surgeon must carefully attach a Keith needle to a suture that is also attached to one end of a cylindrical prosthesis. This threading procedure can be cumbersome and time consuming and may increase the time of the surgical procedure.

After the surgeon threads the needle with the suture, the surgeon places the Keith needle in the Furlow insertion tool and uses the Furlow insertion tool to place the Keith needle and the suture into the corpus cavernosa and then through the glans, by use of the Keith needle to puncture the glans. The needle and suture are then used to apply traction to the cylinder and draw the prosthesis into the corpus cavernosa. Threading the suture into the Keith needle must be done carefully because any kinks in the suture can make it difficult to thread the suture and needle into the Furlow insertion tool.

To install each prosthesis, the threaded Keith needle is placed in the Furlow insertion tool, and the Furlow insertion tool is advanced into the corpus cavernosa until the forward end is inside the crown of the penis, or glans. At this point, the prosthesis and part of the suture attached to the prosthesis remain outside of the body of the patient. The Keith needle is then forced out of the barrel of the Furlow insertion tool, by applying pressure to the obturator. The Keith needle pierces the glans of the penis, and the surgeon grasps the Keith needle from outside of the body and pulls the needle and suture from the penis leaving the suture threaded though the corpus cavernosa. The Furlow insertion tool is then withdrawn from the penis. The suture is then pulled to draw the prosthesis into the incision and thus into the corpus cavernosa. Once the prosthesis is in place, the suture is removed. This procedure is usually performed to install one prosthesis in each corpus cavernosa. After implantation of the prosthesis, the incision at the base of the penis is closed and the hole in the glans from the Keith needle is permitted to close by healing.

SUMMARY

The present invention relates to methods and devices that overcome certain shortcoming of prior penile implant devices and related methods, by providing implantable penile prostheses that include a suture that is connected to a needle and an end of the prosthesis during manufacturing of such a prosthesis. As such, the connection of the suture to the needle can be maintained during a pre-operative storage period of the prosthesis. That is, such a connection is preferably maintained after manufacturing and until a time when the implant device is prepared for surgical implantation. Preferably, such a connection is made during manufacturing and maintained while the penile prosthesis and needle are stored in a package or the like. The penile prosthesis and needle can then be provided to a surgical team in a connected configuration in accordance with the present invention before, during, or after any preparation for surgery is commenced.

In one aspect, the present invention relates to an implantable penile prosthesis. The implantable penile prosthesis includes an implantable cylindrical prosthesis and a suture connected to an end of the penile prosthesis. The suture is also connected to a needle such as a Keith needle. For example, the suture can be threaded through an eye of the needle. The implantable penile prosthesis may also include a sheath for the needle and suture, to hold or cover the needle and suture and prevent tangling. An example can be a sheath that encloses at least a portion of the needle and at least a portion of the suture. The needle may include bends or curves so the needle is not straight, for example to produce friction between the needle and the sheath to prevent the sheath from falling off of the needle. In addition to the sheath, the needle may include a protective cover such as a cap, tube, or sleeve, or other device that functions to cover at least a sharp end of the needle.

In another aspect, the present invention relates to a method of making an implantable penile prosthesis device. The method includes providing an implantable penile prosthesis and connecting a suture to an end of the prosthesis. The method also includes connecting the suture to a needle, such as by threading the suture through an eye of a needle or crimping or swaging the ends of suture portions to a connecting end of the needle. The method can also include inserting the needle and suture into a holder or cover such as a sheath or the like. Optionally, either the piercing end or the eye end of the threaded needle may be inserted into the cover or holder or sheath. Moreover, the needle may include bends or curves so the needle is not straight, for example to produce friction between the needle and the sheath to prevent the sheath from falling off of the needle.

Another aspect of the present invention relates to a method of using an implantable penile prosthesis. The method includes a step of providing an implantable penile prosthesis having a suture that is attached to an end of the penile prosthesis and also attached to a needle. For example, the suture can be threaded through the eye of the needle or otherwise secured to the needle. The needle can be inserted into a Furlow insertion tool, and then the corpus cavernosa of a penis. The needle can be placed through the glans of the penis and used to draw the penile prosthesis, attached to the suture, into the corpus cavernosa of a patient. The needle may include bends or curves so the needle is not straight, for example to produce friction between the needle and the sheath to prevent the sheath from falling off of the needle.

Another embodiment of the present invention relates to a kit that contains a device as described herein, including a prosthesis and a needle connected to each other with a suture connected to the needle at manufacture of the device. The needle and at least a portion of the suture can be held or contained by a sheath or a cover.

Implantable penile prostheses having connected sutures, as described herein, can provide advantages during surgery to install the prostheses. One advantage is that a surgeon does not have to thread a suture through an eye of a needle in the operating room. Thus, handling of the suture by the surgeon can be reduced. This can reduce the possibility of a suture becoming accidentally kinked. As described in the Background section, such kinking of a suture is undesirable because it can make it difficult to thread the suture into a Furlow insertion tool. With the presently-described penile prostheses, two sutures and two cylindrical prostheses are involved. Thus, two sutures would otherwise have to be threaded. The present invention avoids the need for a surgeon to thread the sutures of both prostheses through the eye of a needle.

A specific result of eliminating the need for a surgeon to thread the sutures through the eye of a needle during surgery, is to reduce the overall time of the surgical procedures by eliminating the time taken to thread one or more (generally two) needles with a suture.

Another advantage of the present invention is that a pre-threaded needle and suture can be provided with a cover or holder or sheath. The suture contained within the sheath can be kept straight and protected, thus making threading of the suture into a Furlow insertion tool, during surgery, much easier. The point of the needle can also be protected so it will not harm any components in the package. The sheath can be used for such a protective function or a separate device such as another sheath, or tube, or cap may be provided for covering at least a sharp end of the needle. With such an arrangement, a surgeon can remove the sheath or protective cap easily and quickly.

DETAILED DESCRIPTION

Figure 1:
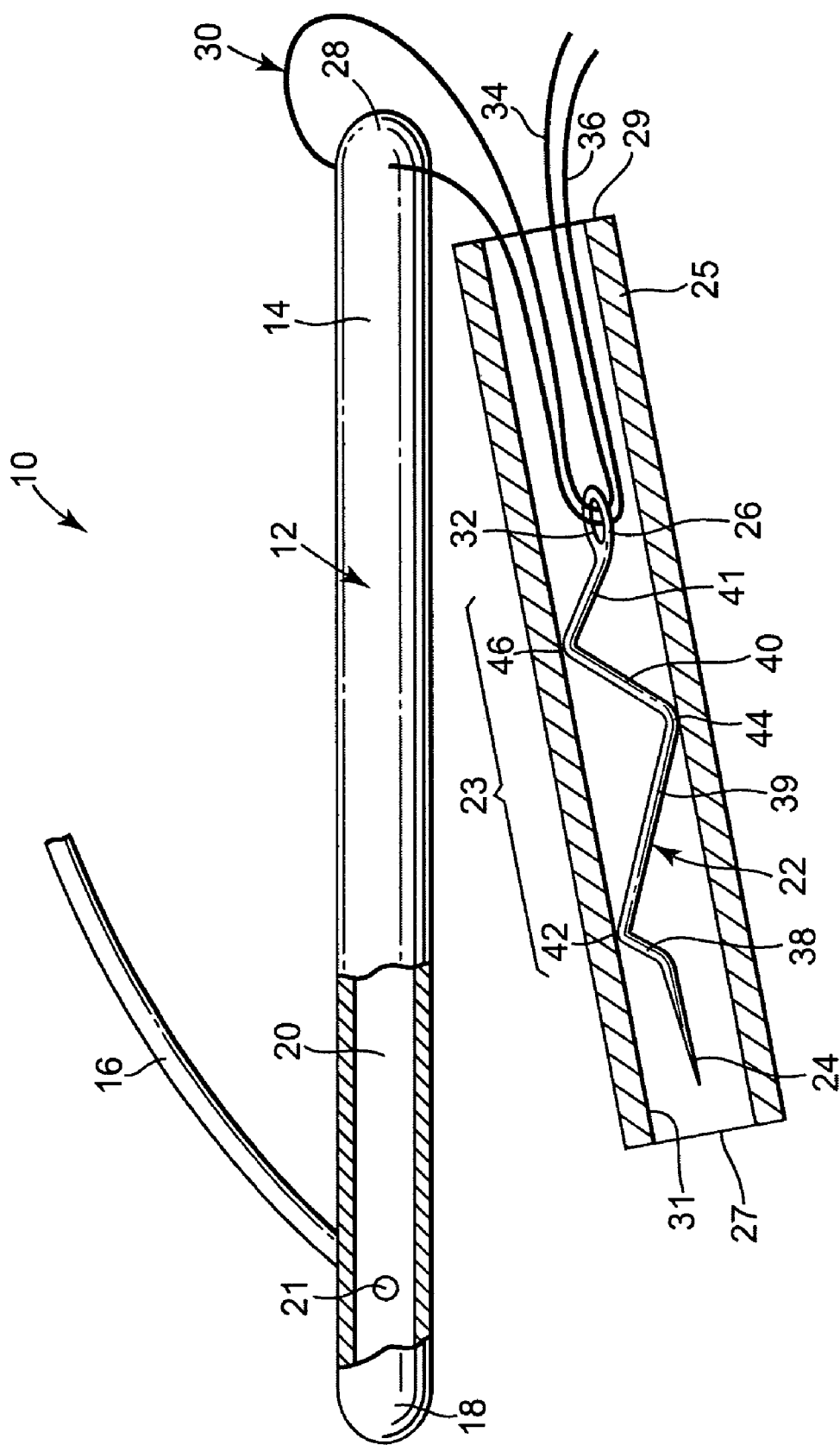
FIG. 1 is a schematic view of a penile implant device of the present invention showing a suture attached to an end of a penile prosthesis of the penile implant device and threaded through a needle positioned within a sheath in accordance with the present invention.

With reference to FIG. 1 an exemplary penile implant device 10 according to the present invention is shown. As illustrated, implant device 10 includes a penile prosthesis 12 that can be implanted in the corpus cavernosa of the penis of a patient for the treatment of impotence. The exemplary penile prosthesis 12 includes a body portion 14 that is cylindrically shaped and inflatable. The body portion 14 of the penile prosthesis 12 is typically formed from silicone or the like and is preferably formed to anatomically fit the corpus cavernosa of a receiving patient. As shown, the body portion 14 of the penile prosthesis 12 includes a tube 16 positioned near a base end 18 of the body portion 14. The tube 16 is in fluid communication with an interior cavity 20 of the body portion 14 by an inlet opening 21 and can be used to supply and remove an inflation fluid to the interior cavity 20 of the body portion 14 in order to inflate and deflate the body portion 14 of the penile prosthesis 12. Such inflation and deflation of the body portion 14 of the penile prosthesis 12 can thus provide and remove an erection in the penis in which the penile prosthesis 12 is implanted. Systems and devices for providing an inflation fluid to the interior cavity of the body portion 14 are known in the art and generally include a fluid-filled reservoir with a pump and valve assembly that can be operatively connected to the tube 16 of the body portion 14 of the penile prosthesis 12. The implant device 10 can be used with any such devices in accordance with the present invention.

As illustrated, the implant device 10 also includes a needle 22 that has a piercing end 24 and a connecting end 26 opposite the piercing end 24. Preferably, the needle 22 comprises a needle that can be used to pierce human tissue, such as a Keith needle or the like. Needles that can be used as the needle 22 may be straight, bent, or curved and exemplary needles are described, for example, in Assignee's copending U.S. patent application Ser. No. 10/375,800, filed Feb. 26, 2003, entitled "Keith Needle for Furlow Insertion Tool," the entire disclosure of which is incorporated herein by reference for all purposes. As shown, the needle 22 comprises a non-straight or bent portion 23 between the piercing end 24 and the connecting end 26. The non-straight portion 23 can help to hold a sheath 25 (as shown in cross-section) relative to the needle 22. As shown, the sheath 25 includes a first end 27, a second end 29, and an inside surface 31. The functional aspects of the sheath 25 and the non-straight portion 23 of the needle 22 are described in greater detail below.

As shown, the needle 22 is connected to a tip end 28 of the body portion 14 of the penile prosthesis 12 by a suture 30. The suture 30 is shown threaded through the tip end 28 of the body portion 14 of the penile prosthesis 12. However, the suture 30 can be connected to the tip end 28 of the body portion 14 in any functional manner in accordance with the present invention. As illustrated in the exemplary implant device 10, the suture 30 passes through the tip end 28 of the body portion 14 and is threaded through an eye 32 at the connecting end 26 of the needle 22. Thus, as shown, the suture 30 comprises first and second suture portions, 34 and 36 respectively, that extend out of the tip end 28 of the body portion 14 and pass through eye 32 of the needle 22. While the suture 30 is shown connected to the needle 22 by threading the suture 30 through the eye 32 of the needle 22, other techniques for connecting the suture 30 to the needle 22 are contemplated and described in greater detail below. For example, the suture portions, 34 and 36, can be threaded through the eye 32 of the needle 22 and tied to the needle 22 to form a knot or the suture portions, 34 and 36, can be tied together or otherwise connected to form a loop that is threaded through the eye 32 of the needle 22. Also, the suture portions, 34 and 36, can be captured by a mechanical device such as a collapsible or crimpable structure or the like to connect any desired portion of the suture 30 to the connecting end 26 of the needle 22. In any case, the suture 30 is preferably connected, attached, or otherwise secured to the needle 22 so that the needle 22 can guide the suture 30 through a corpus cavernousum of a penis and out through the glans of the penis for implantation of the penile prosthesis 12.

As shown in FIG. 1, the suture 30 is threaded through the eye 32 of the needle 22 so that the first and second suture portions, 34 and 36 respectively, double back and exit the second end 29 of the sheath 25. Preferably, the ends of the suture portions, 34 and 36, extend from the second end 29 of the sheath 25 by a length that can be grasped and held by a surgeon. As such, ends of the suture portions 32 and 34 can be held while the sheath 25 is pulled away to expose the remainder of the suture 30 and the needle 22 in order to prepare the implant device 10 for implantation as described in more detail below.

Figure 2:
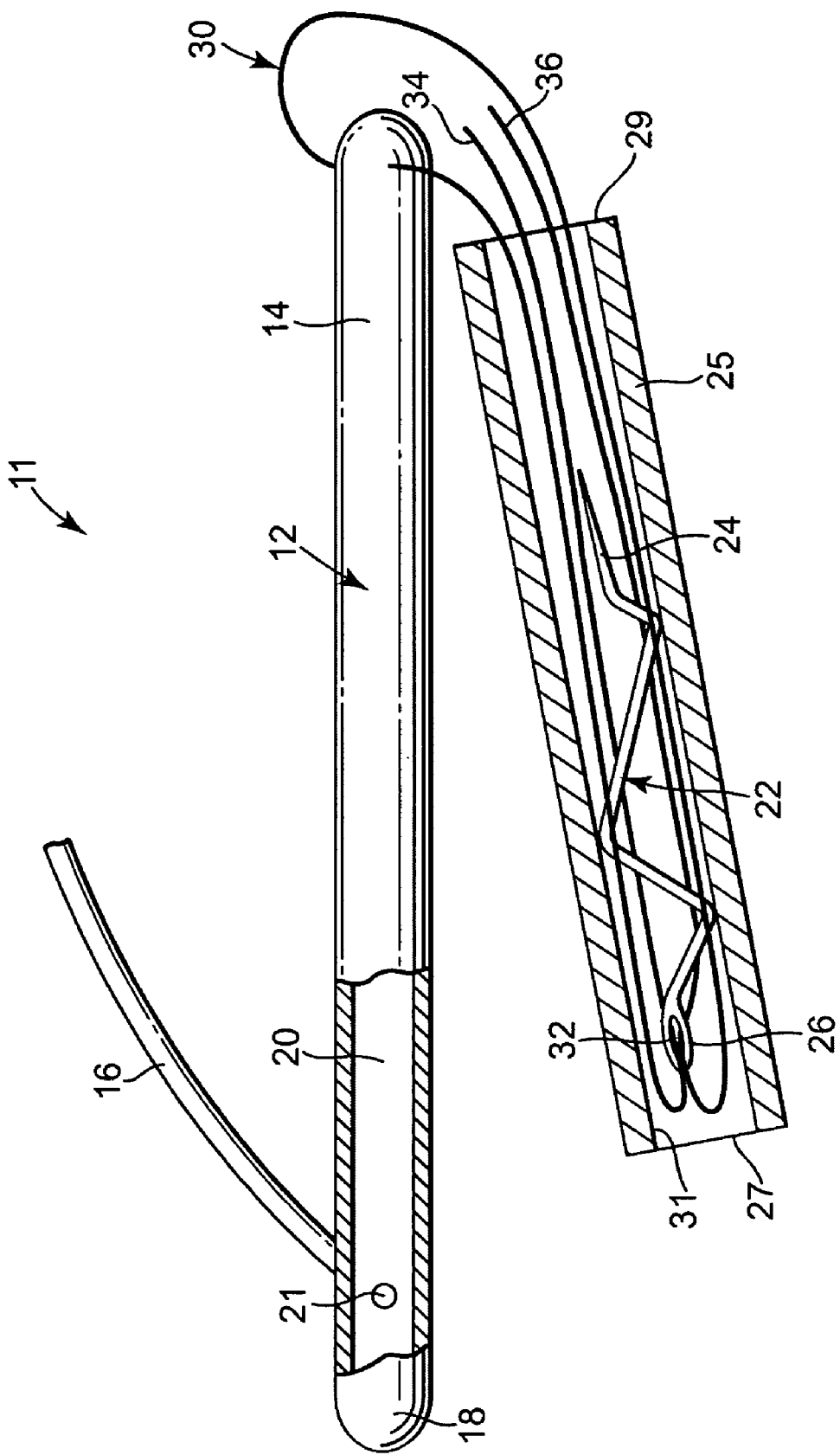
FIG. 2 is a schematic view of the penile implant device of FIG. 1, showing the needle in a reversed position within the sheath with respect to the position of the needle shown in FIG. 1.

Also, as illustrated, the needle 22 is positioned within the sheath 25 so that the piercing end 24 of the needle 22 corresponds with the first end 27 of the sheath 25 and the connecting end 26 of the needle 22 corresponds with the second end 29 of the sheath 25. However, the position of the needle 22 relative to the sheath 25 may be reversed. For example, another penile implant device 11 is shown in FIG. 2. The implant device 11 includes all of the components of the implant device 10 shown in FIG. 1 except that the position of the needle 22 relative to the sheath is reversed. In particular, the needle 22 is positioned within the sheath 25 so that piercing end 24 of the needle 22 corresponds with the second end 29 of the sheath 25 and the connecting end 26 of the needle 22 corresponds with the first end 27 of the sheath 25.

If the connecting end 26 of the needle 22 is inserted into the sheath 25 first, such as is illustrated in FIG. 2, a shorter length of sheath 25 can be used. The connecting end 26 of the first design can also hold the needle 22 firmly in the sheath 25, because plural strands (four in this case) of suture 30 can pass by the needle 22 and add to the interference between needle 22 and the inside surfaces of the sheath 25. In any case, the suture 30 can be coiled, bunched, or folded so that a plurality of suture strands or portions can be held by the sheath 25.

If the piercing end 24 of the needle 22 is inserted into the sheath 25 first, such as illustrated in FIG. 1, a longer length of the sheath 25 can be used for the same suture length used in the connecting end first design. This is because the suture 30 is not pulled into the sheath 25 as far as the needle 22. Also, the needle 22 might not be held as firmly because the suture 30 does not pass by the needle 22. To hold the needle 22 more firmly with this design a smaller diameter sheath (from 1 to 1.5 mm, for example) may be used, if desired. One advantage to such a design is that because the connecting end 26 of the needle 22 is leading as the needle 22 is being pulled out for use in the operating room, the needle 22 cannot undesirably become stuck in the sheath 25.

In accordance with the present invention, the needle 22 is connected to the body portion 14 of the penile prosthesis 12 before implantation surgery. That is, the needle 22 is pre-connected or pre-attached to the body portion 14 of the penile prosthesis 12 during manufacture and assembly of the implant device 10. The implant device 10 can be provided to a surgeon in a configuration that is ready to implant, such as in a kit or the like, and the surgeon does not need to connect the penile prosthesis 12 to the needle 22 in the operating room. This can help to prevent kinking or tangling of the suture and can minimize the length of the surgical procedure. Because the implant device 10 will be stored for some period of time after assembly and before surgery, the present invention provides implant devices, such as the implant device 10, that can maintain the connection between a needle and a penile prosthesis during a storage or pre-operative period of the implant device.

The sheath 25 is preferably designed so that the sheath 25 helps to maintain the connection between the needle 22 and the body portion 14 of the penile prosthesis 12 during a pre-operative storage period of the implant device 10. In particular, the sheath 25 can hold the needle 22 and connected suture 30 during handling that occurs during manufacturing and packaging of the implant device 10, and also during handling of the implant device 10 that occurs by the user, for example, prior to installation of the penile prosthesis 12 during surgery.

As illustrated, the sheath 25 comprises an elongate tube that is preferably designed to contain at least a portion of the needle 22 and at least a portion of the suture portions, 34 and 36, for maintaining the connection between the needle 22 and the body portion 14 in accordance with the present invention. Any number of sheaths can be used whether overlapping, abutting, joined, or otherwise positioned relative to each other. Moreover, the sheath 25 is preferably designed so that it can be easily removed at the time the penile prosthesis 12 of the implant device 10 is implanted. Preferably, the sheath 25 fits over the needle 22 and suture portions, 34 and 36, so that the sheath 25 can prevent inadvertent displacement of the needle 22 from the suture portions, 34 and 36, when the needle 22 and suture portions, 34 and 36, are positioned inside of the sheath 25. As such, at least a portion of the sheath 25 preferably comprises a suitable material that can cause at least a portion of the inside surface 44 of the sheath 25 to contact at least a portion of the needle 22 and the suture portions, 34 and 36, in a resistive manner for holding the needle 22 and suture portions, 34 and 36, relative to each other.

In particular, as shown in FIG. 1, the non-straight portion 23 of the needle 22 includes portions 38, 39, 40, and 41. Portions 38 and 39 are provided at an angle relative to each other to form an apex 42, portions 39 and 40 are provided at an angle relative to each other to form an apex 44, and portions 40 and 41 are provided at an angle relative to each other to form an apex 46. Preferably, the non-straight portion 23 of the needle 22 and the sheath 25 are designed so that the apexes 42, 44, and 46 contact the inside surface 31 of the sheath 25 for holding the needle 22 and the sheath 25 relative to each other. Preferably, as shown, the inside surface 31 of the sheath 25 touches the apexes 42, 44, and 46 to provide a holding fit between the sheath 25 and the needle 22 such as by resistive frictional engagement. The sheath 25 also preferably holds the suture portions 34 and 36 in place to prevent the needle 22 from becoming inadvertently disconnected from the penile prosthesis 12. Preferably, the inside surface 31 of the sheath 25 helps to provide some resistance (frictional, for example) to the suture portions, 34 and 36, against each other and/or against some portion of the needle 22 for holding the suture portions, 34 and 36, so that the suture portions, 34 and 36, do not slip out of the eye 32 of the needle 22 during handling that occurs during manufacturing and packaging of the implant device 10, and also during handling that occurs by the user, for example, prior to installation of the penile prosthesis during surgery.

The particular material, inside diameter, wall thickness, and/or length of the sheath 25 may be selected as based upon the particular size and shape of the needle 22, including whether the needle 22 is straight, bent, or curved, and if so, to what degree, as well as the gauge and/or length of the suture portions 34 and 36. The sheath 25 can be formed from lightweight plastic or other polymeric materials, such as silicone in the form of a thin flexible silicone tube that can be positioned in holding contact with at least a portion of the needle 22 and the suture portions, 34 and 36. The sheath 25 may comprise any material that can function to cover at least a portion of the needle 22 and preferably help to maintain the connection between the needle 22 and the suture 30. For example, plastics, metal foils, papers and linens may be used in accordance with the present invention. Such materials may be elastic or inelastic and any combination of materials may be used.

Where the needle 22 comprises a typical Keith needle or the like and the suture portions, 34 and 36 have a length sufficient for use with a Furlow insertion tool or the like, the exemplary sheath 25 is preferably 10 to 40 centimeters (cm) in length, more preferably 20 to 30 cm in length. Likewise, the inside diameter of the sheath 25 is preferably 1 to 2 millimeters (mm). For a typical straight Keith needle, the inside diameter of the sheath 25 is preferably 1 to 1.5 mm. For a typical bent or curved Keith needle, the inside diameter is preferably 1.4 to 1.6 mm. Dimensions outside of these ranges may also be useful depending on the size and shape of the particular needle design that is used. In any case, the inside diameter of the sheath 25 preferably accommodates the particular needle structure in accordance with the present invention whether the needle is straight, curved, or bent.

It is contemplated that any mechanism, device, or holding means can be used to hold the needle 22 and the suture 30 in a similar functional manner as the sheath 25. For example, holding devices that comprise squeezing clamping or adhesive holding aspects may be used to hold the needle 22 and suture 30 relative to each other in accordance with the present invention. Moreover, it is contemplated that releasable adhesives, tapes, wires, elastic bands, and the like may be used to provide such a holding function in accordance with the present invention.

Figure 17:
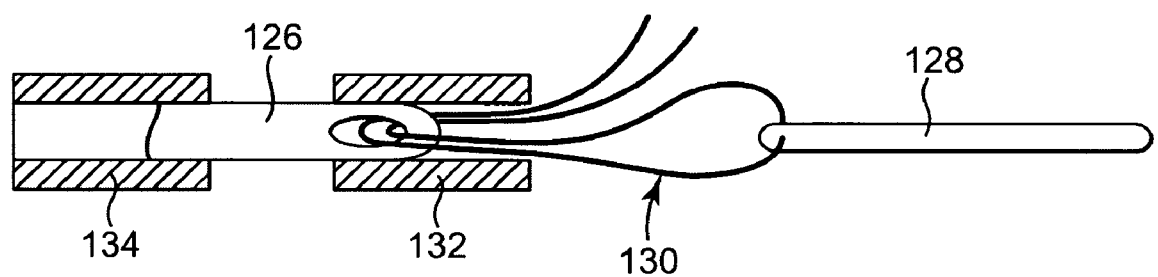
FIG. 17 is a schematic view of a penile implant device of the present invention showing in particular a suture connected to an end of a penile prosthesis and also connected to a needle and having a sheath covering a portion of the needle and suture and a protective cap positioned on a sharp end of the needle in accordance with the present invention.

The sheath 25 can also be used to protect the needle 22 and/or suture 30. For example, the sheath 25 can extend over the piercing end 24 of the needle 22 to provide such a protective function with or without the sheath 25. Also, a separate device may be used to provide such a protective function. For example, in FIG. 17 a needle 126 is shown connected to a penile prosthesis 128 by a suture 130. A sheath 132 is shown and can be used to hold the suture 130 relative to the needle 126 in accordance with the present invention and as described above. As shown, a protective cap 134 covers and protects the sharp end of the needle 126. The protective cap 134 may include any device that can function to protect the sharp end of the needle 126 from damage or from undesirably contacting someone or something such as a plug, cap, or covering device such as tape or the like. Preferably, a protective cap can be easily removed to gain access the needle. The protective cap 134 may include anything that may be used as a sheath in accordance with the present invention. Also, while the protective cap 134 and sheath 132 are shown spaced from each other so that a portion of the needle 126 is exposed, such a configuration is exemplary and for illustrative purposes and in not required. The protective cap 134 and sheath 132 may be butted against each other so that the entire needle 126 is enclosed and protected. Also, a protective cap that fits into and closes an end of a sheath, such as the end 27 of the sheath 25 shown in FIGS. 1 and 4 may be used. In any case, a protective cap may be provided in any manner such that the protective cap covers or helps to cover at least a sharp portion of a needle alone or together with a sheath or the like.

A device of the present invention such as implant device 10 of FIG. 1 can be assembled by threading the suture 30 through the eye 32 of the needle 22 and inserting either the piercing end 24 or the connecting end 26 of the needle 22 into the sheath 25. As the needle 22 is advanced into the sheath 25, the suture 30 preferably follows until the second end 29 of the sheath 25 is snug or close to snug against the tip end 28 of the body portion 14. If the sutures are attached by mechanical or adhesive components, an attachment step can be used in place of the step of threading the suture 30 through the eye 32 of the needle 22.

In accordance with the present invention, a needle can be connected to a penile prosthesis by a suture in any manner so that the needle can guide the suture through a corpus cavernousum of a penis and out through the glans of the penis during implantation of the penile prosthesis. As such, the connection between the needle and the suture should have sufficient strength to withstand the tensile forces applied to the connection during surgical implantation of the penile prosthesis. Also, the connection between the needle and the suture is preferably streamlined so that when the portion of the needle where the suture connection is made is pulled through the glans of the penis, resistance and potential tissue damage are minimized. Accordingly, in FIGS. 3-8 several exemplary connections in accordance with the present invention are illustrated and described in detail below.

Figure 3:
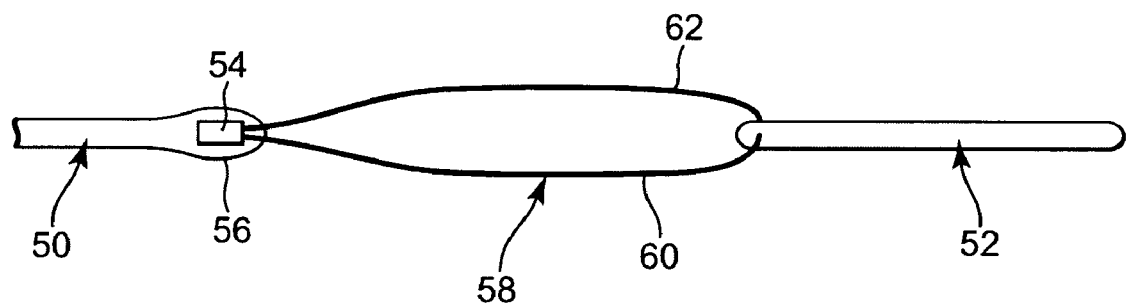
FIG. 3 is a schematic view of a penile implant device of the present invention showing in particular a suture connected to an end of a penile prosthesis and also connected to a needle by a connecting device in accordance with the present invention.

In FIG. 3 an exemplary technique for providing a connection between a needle 50 and a penile prosthesis 52 is illustrated. Such a technique can also be used for maintaining a connection between the needle 50 and the penile prosthesis 52 during a storage or pre-operative period of an implant device in accordance with the present invention. That is, such a connection is preferably maintained after manufacturing and until a time when the implant device is prepared for surgical implantation. Preferably, such a connection is made during manufacturing and maintained while the penile prosthesis and needle are stored in a package or the like. The penile prosthesis and needle can then be provided to a surgical team in a connected configuration in accordance with the present invention before, during, or after any preparation for surgery is commenced.

While a straight needle is illustrated as the needle 50, any needle having any structure whether straight, curved or bent can be used. As illustrated, the needle 50 includes a connecting device 54 (schematically shown) at a connecting end 56 of the needle 50. A suture 58 is connected to the penile prosthesis 52. The suture 58 includes first and second suture portions, 60 and 62, that are connected to the needle 50 by the connecting device 54. As such, each of the suture portions, 60 and 62, forms a connection to the penile prosthesis 52.

The connecting device 54 is preferably designed to provide a connection between the needle 50 and the suture 58 that has sufficient strength for implanting the penile prosthesis 52. As such, the connecting device 54 may include any mechanical device or structure that can hold, capture, or otherwise engage with a suture in accordance with the present invention such as by crimping, swaging, clamping, and/or adhesive bonding, or the like. The connecting device may form a permanent connection or may be a releasable connection. Also, it is contemplated that a sheath, such as the sheath 25 described above, or similarly functioning device, may be used to help to maintain a connection between the needle 50 and the penile prosthesis 52. Moreover, the sheath 25 can be used for a protective function to protect any portion of a needle and suture as mentioned above.

Figure 4:
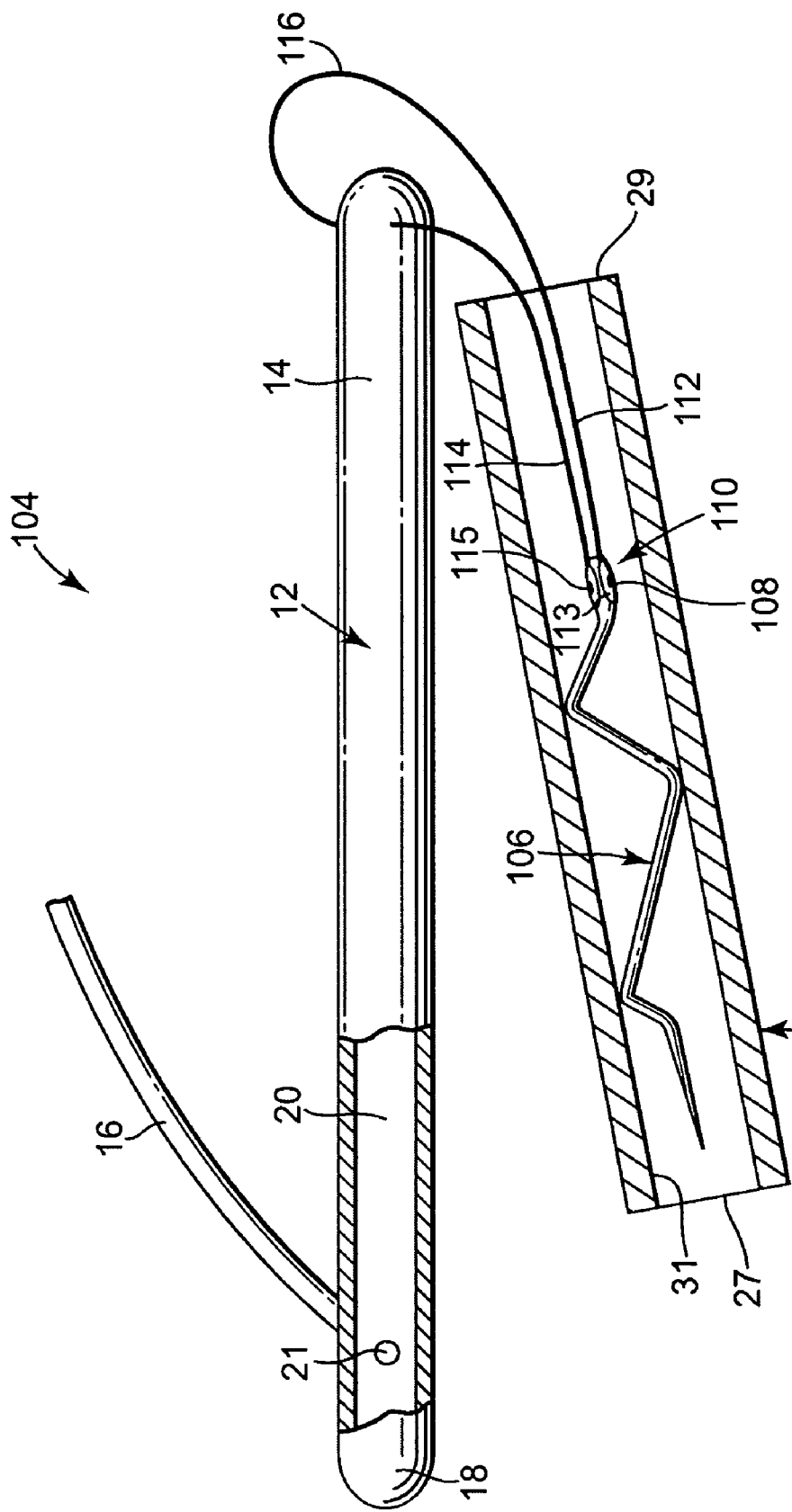
FIG. 4 is a schematic view of a penile implant device of the present invention showing in particular a suture connected to an end of a penile prosthesis and also connected to a needle by a crimping device.

As an example of an embodiment with a sheath and a mechanical attachment, FIG. 4 shows a penile implant device 104. The penile implant device 104 includes the penile prosthesis 12 and sheath 25 described above with respect to FIGS. 1 and 2. The penile implant device 104 include a needle 106 having a crimping structure 108 at a connecting end 110 of the needle 106 that bends around ends of suture portions 112 and 114 of suture 116 to secure the ends of suture portions 112 and 114 to the needle 106.

The crimping structure 108 is illustrated to include first and second portions 113 and 115, each of the first and second portions, 113 and 115, being folded over each of the ends of suture portions 112 and 114. Any alternative structure may be used to cause the suture ends to be secured to the connecting end of the needle, including alternative structures that are known for suture needles (i.e., needles that are known in the surgical arts and that include suture ends pre-secured to the blunt end of a surgical needle). As an example of one alternative embodiment, a structure could be used that includes one piece of material at the connecting end of the needle that folds over and secures both of the suture string ends at the same time (instead of two structures as illustrated in FIG. 4). As another alternative, a circular crimp could be used that includes a set of two pieces of crimping material at the connecting end of the needle that together form a circle into which the ends of the suture portions can be inserted and which can then be crimped together to secure the ends to the needle. Still different yet, if desired, other methods of attachment might be used, such as a different mechanical structure optionally separate from the needle structure, a knot, or a useful adhesive.

In FIGS. 5-8, a needle 64 having an eye 66 at a connecting end 68 and a penile prosthesis 70 are illustrated and various techniques to connect the needle 64 to the penile prosthesis 70 in accordance with the present invention are shown and described below. These connection techniques can be used to maintain the connection between the needle 64 and the penile prosthesis 70 during a storage or pre-operative period of an implant device. The needle 64 is exemplary and any needle whether straight, bent, or curved may be used with any of the connection techniques described herein. For example, the needle 22 described above can be used. Also, the penile prosthesis 70 is exemplary and any penile prosthesis may be used such as the penile prosthesis 12 described above as well as those known in the art. Also, it is contemplated that a sheath, such as the sheath 25 described above, or similarly functioning device, may be used to help to maintain a connection between the needle 50 and the penile prosthesis 52. Moreover, the sheath 25 can be used for a protective function to protect any portion of a needle and suture or another device such as with the protective cap described above with respect to FIG. 17. For example, a first sheath may be used for a holding function and a second sheath (or other device that can protect the needle) may be used for a protecting function. Preferably a sheath is used to substantially enclose a needle and a protective cap or the like is used to close off the end of the sheath having the sharp end of the needle. For example, a protective cap may be used to close the end 27 of the sheath 25 shown in FIGS. 1 and 4 and as described above.

Figure 5:
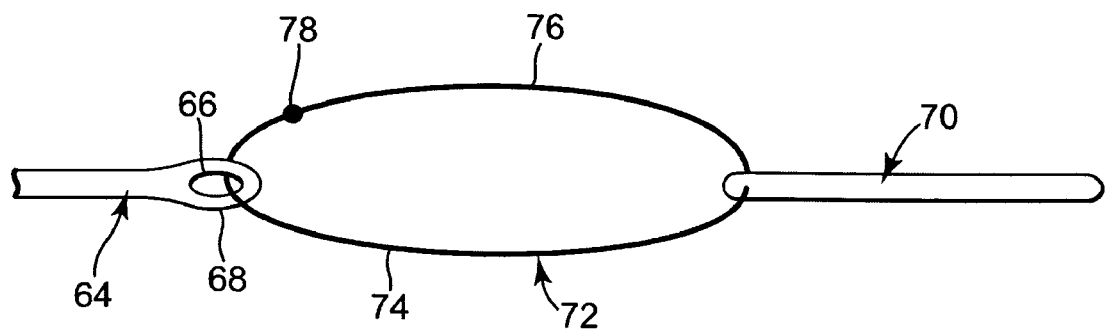
FIG. 5 is a schematic view of a penile implant device of the present invention showing in particular a suture connected to an end of a penile prosthesis wherein the suture includes first and second suture portions joined by a knot to form a suture loop that is connected to a needle in accordance with the present invention.
Figure 6:
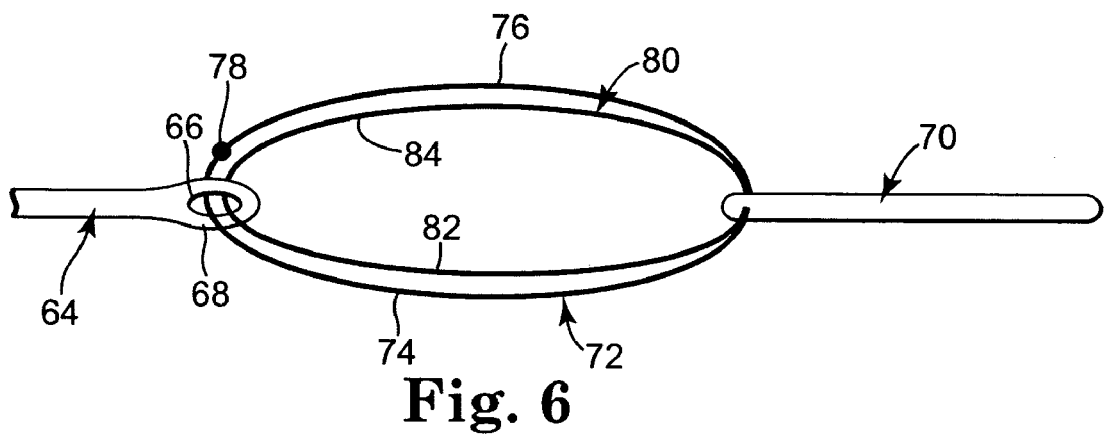
FIG. 6 is a schematic view of the penile implant device of FIG. 4 showing in particular an additional suture loop connecting the needle to the penile prosthesis in accordance with the present invention.
Figure 7:
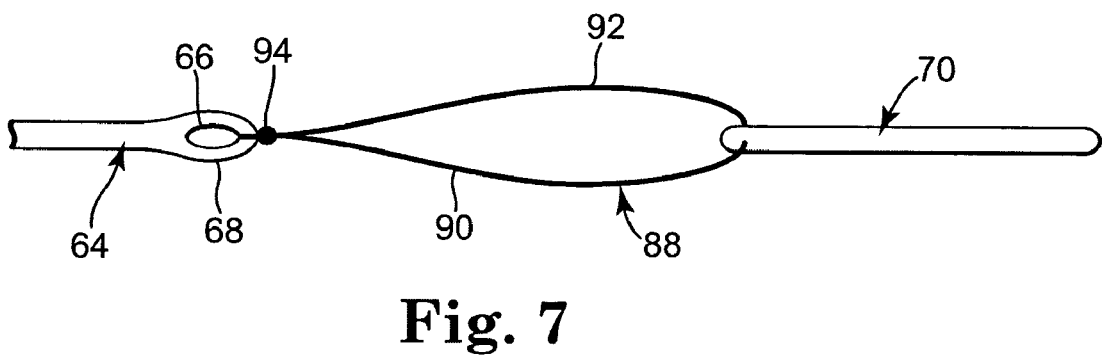
FIG. 7 is a schematic view of a penile implant device of the present invention showing in particular a suture connected to an end of a penile prosthesis and also connected to a needle with a knot in accordance with the present invention.

With reference to FIG. 5, the needle 64 is connected to the penile prosthesis 70 by a suture 72, as shown. The suture 72 is threaded through the penile prosthesis 70, as shown, so that first and second suture portions 74 and 76 extend out of the penile prosthesis 70. The first suture portion 74 passes through the eye 66 of the needle 64 and is joined with the second suture portion 76 by a knot 78. As such, the first and second suture portions, 74 and 76, are tied together to form a loop, as illustrated. In accordance with the invention, the suture portions, 74 and 76, may be joined together to form such a loop in any manner that provides sufficient strength for implanting the penile prosthesis 70. For example, the suture portions, 74 and 76, may be fused together such as by thermal or ultrasonic welding or the like. The suture portions, 74 and 76, can be also be joined by using a mechanical device that can capture and hold each of the suture portions, 74 and 76, such as a sleeve that can receive each of the suture portions, 74 and 76, which can be crimped or collapsed to positively engage with the suture portions, 74 and 76. Moreover, an adhesive, alone or in combination with another holding or joining technique, can be used to join the suture portions, 74 and 76, together in accordance with the present invention.

Preferably, the knot 78 is positioned relative to the connecting end 68 of the needle 64 so that the knot 78 passes through the glans of the penis together with the needle 64 when the needle 64 is pulled through the glans of the penis (in a streamlined manner). As such, the knot 78 is preferably in close proximity to the connecting end 68 of the needle 64. For example, the knot 78 is preferably positioned so that the knot 78 is just behind the connecting end 68 of the needle 64 and follows the connecting end 68 of the needle 64 when the needle 64 is pulled through the glans of the penis during implantation of the penile prosthesis 70. By positioning the knot 78 in such a manner, the knot 78 can pass through the opening created in the glans of the penis by the needle 64 with reduced resistance. In any case, to minimize or reduce trauma, the knot 78 is preferably positioned so that knot 78 can be pulled through the glans of the penis together with the needle 64 rather than being pulled through the glans of the penis when the suture is removed from the penile prosthesis 70 after implantation of the penile prosthesis 70.

The knot 78 is preferably provided to have sufficient knot break strength and sufficient resistance to slipping (that would cause the knot 78 to become partially or fully untied) for implanting the penile prosthesis 70 in accordance with the present invention. Preferably, the knot 78 is provided to withstand a predetermined tensile force applied to the knot 78. For example, for implantation of a typical penile prosthesis such as the penile prosthesis 70, the knot 78 should be able to resist breaking or slipping when a tensile force of ten pounds is applied to the knot 78. However, any predetermined force can be used to qualify the knot 78 as determined by considering the particular penile prosthesis to be implanted, the design of the knot 78, or the design of the connecting end of needle 64.

Any knot type can be used for the knot 78. Moreover, any number of knots can be used. Preferably the cross-sectional size or shape of knot 78 is minimized so that the knot 78 can easily pass through the opening created in the glans of the penis by the needle 64. Preferably, the cross-section of the knot 78 is less than or equal to the cross-section of the connecting end 68 of the needle 64. That way, when the knot 78 is close to the connecting end 68 of the needle 64, the knot 78 can pass through the opening formed in the glans of the penis by the needle 64 without significant resistance. The knot 78 can be streamlined in any desired way including covering or coating the knot 78 in a manner that reduces resistance or drag. For example, the knot 78 could be enclosed in a tapered sleeve or the like.

Figure 9:
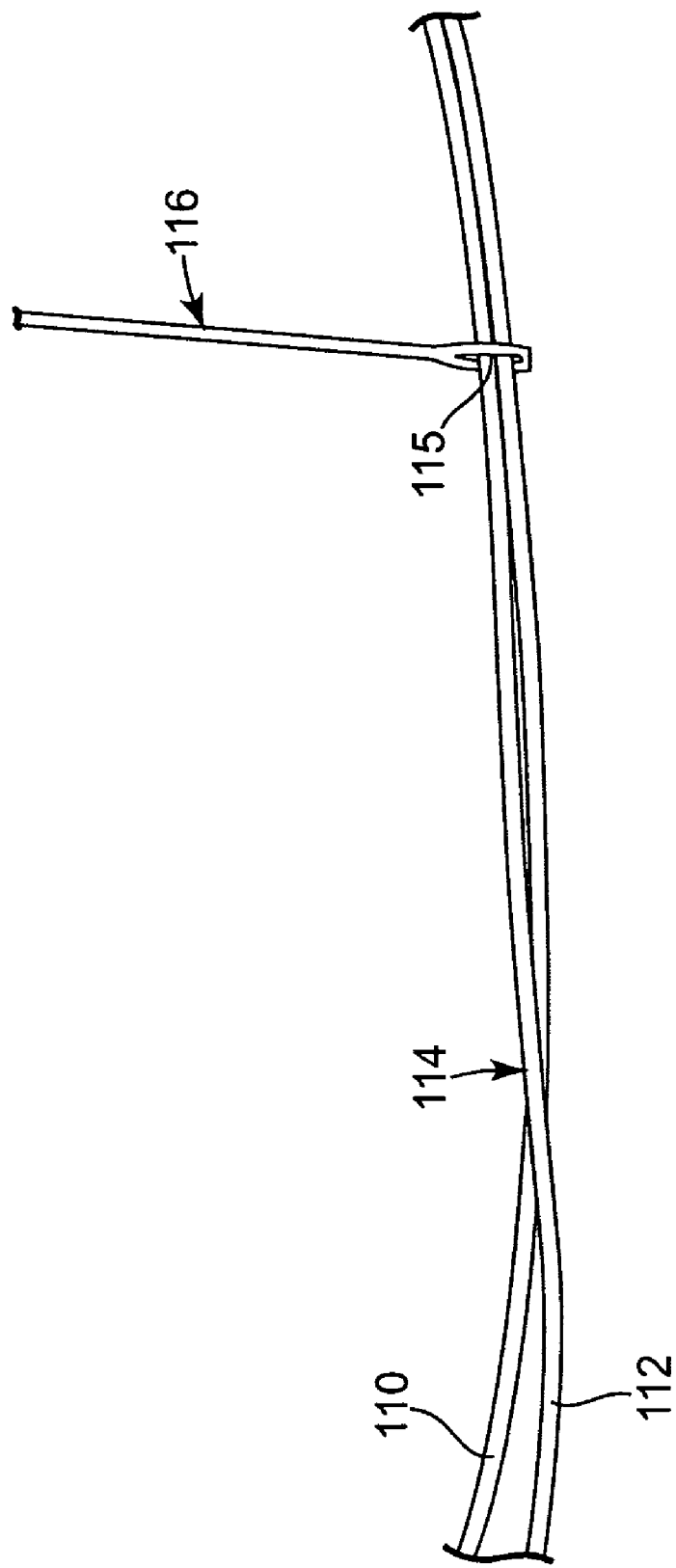
FIG. 9 is a schematic view of a step for connecting a suture to a needle with a knot in accordance with the present invention showing in particular first and second suture portions threaded through an eye of a needle.
Figure 10:
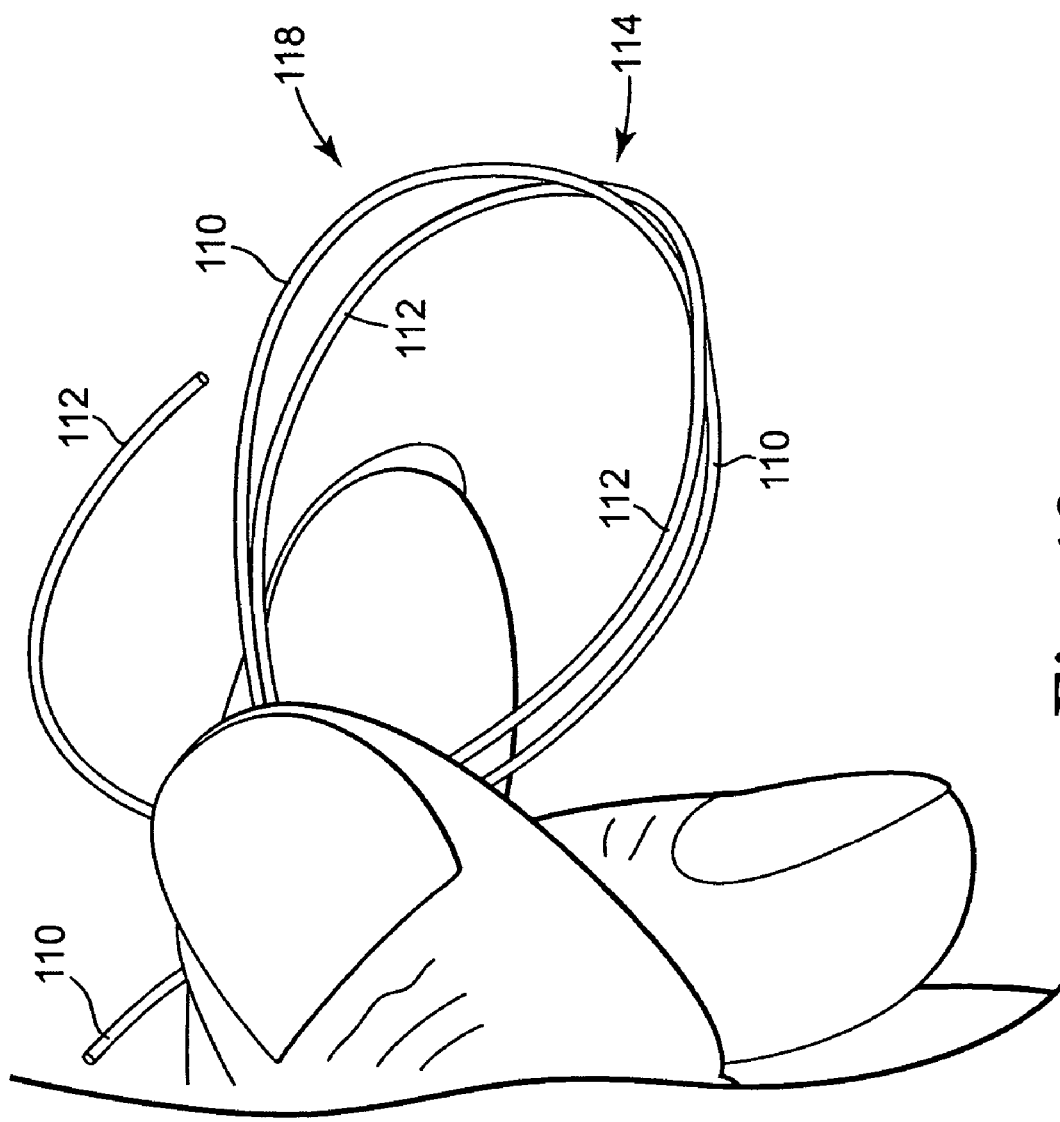
FIG. 10 is a schematic view of another step for connecting a suture to a needle with a knot in accordance with the present invention showing in particular a step of forming a loop with the first and second suture portions.
Figure 11:
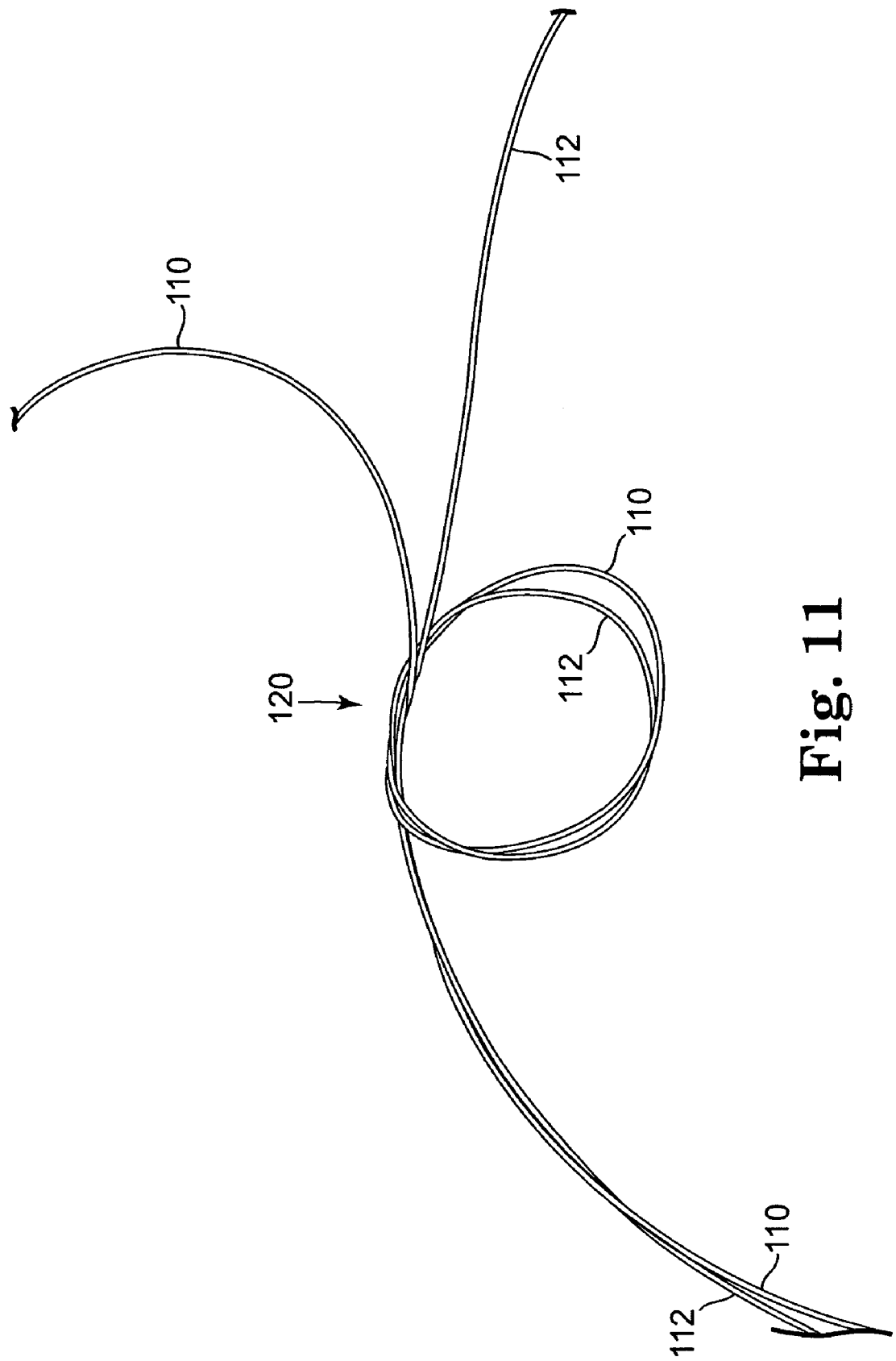
FIG. 11 is a schematic view of another step for connecting a suture to a needle with a knot in accordance with the present invention showing in particular a step of passing the first and second suture portions through the loop of FIG. 10 to form a loose knot.
Figure 12:
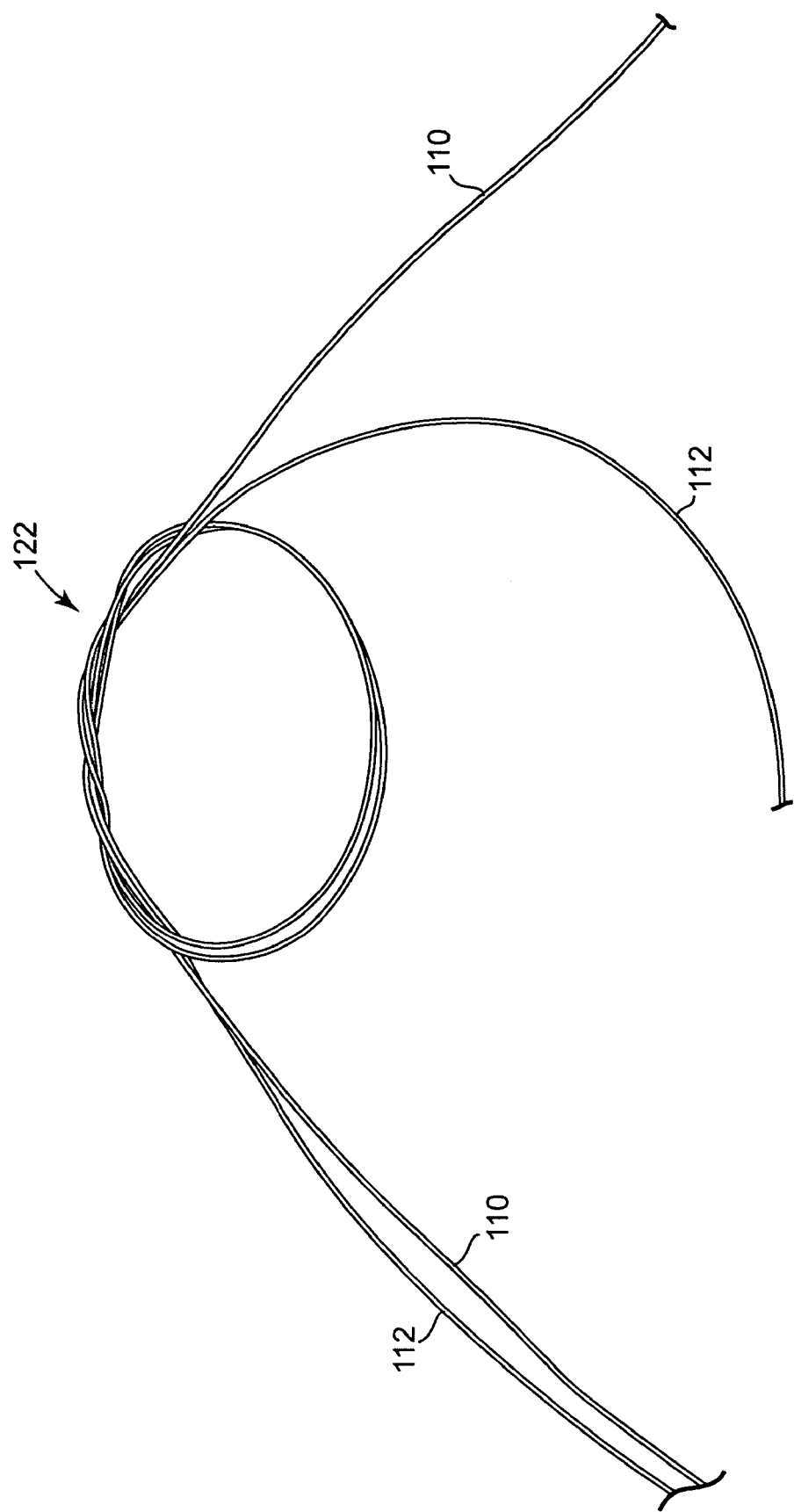
FIG. 12 is a schematic view of another step for connecting a suture to a needle with a knot in accordance with the present invention showing in particular a step of passing the first and second suture portions through the loose knot of FIG. 11.
Figure 13:
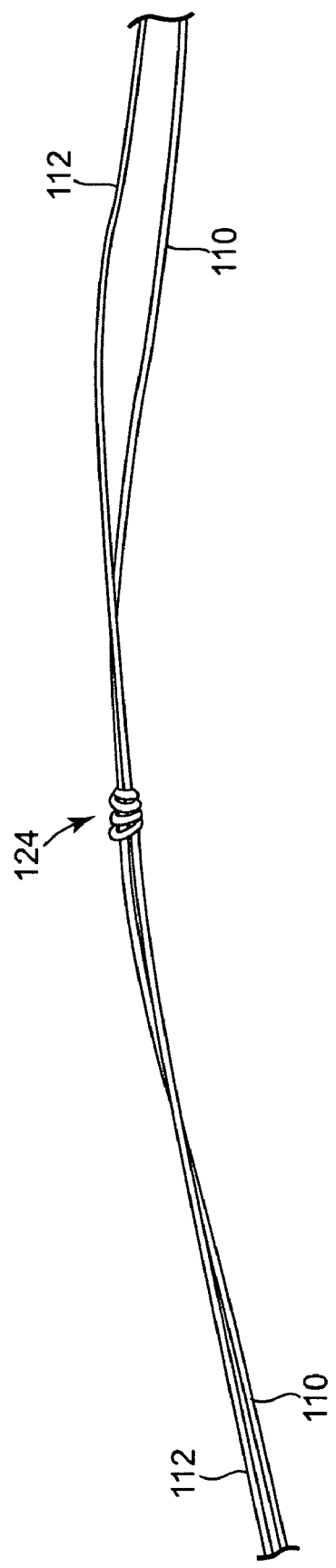
FIG. 13 is a schematic view of another step for connecting a suture to a needle with a knot in accordance with the present invention showing in particular a step of tightening the loose knot of FIG. 12.
Figure 14:
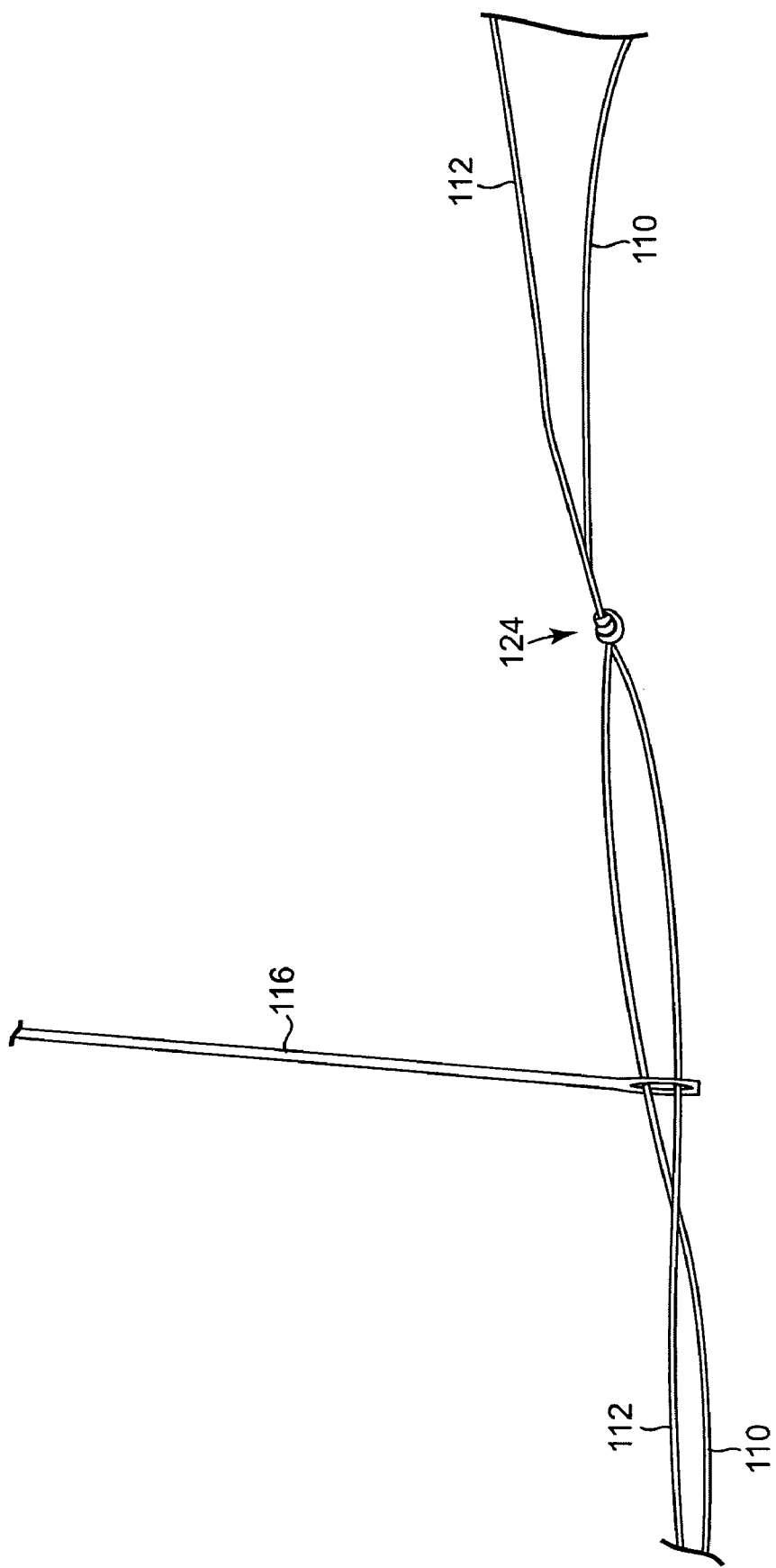
FIG. 14 is a schematic view of another step for connecting a suture to a needle with a knot in accordance with the present invention showing in particular a step of spacing the knot of FIG. 13 from the needle.
Figure 15:
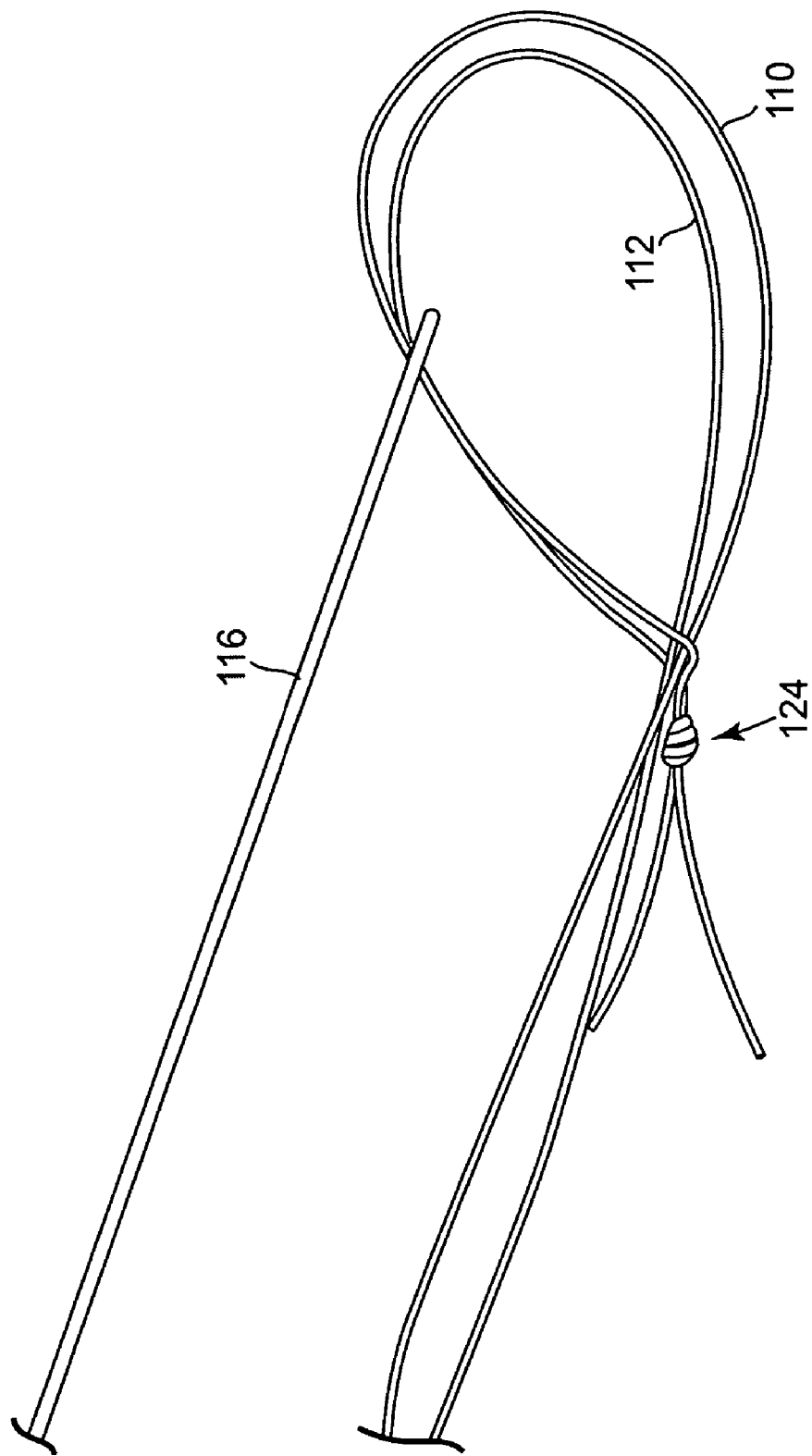
FIG. 15 is a schematic view of another step for connecting a suture to a needle with a knot in accordance with the present invention showing in particular a step of passing the needle through the first and second suture portions.
Figure 16:
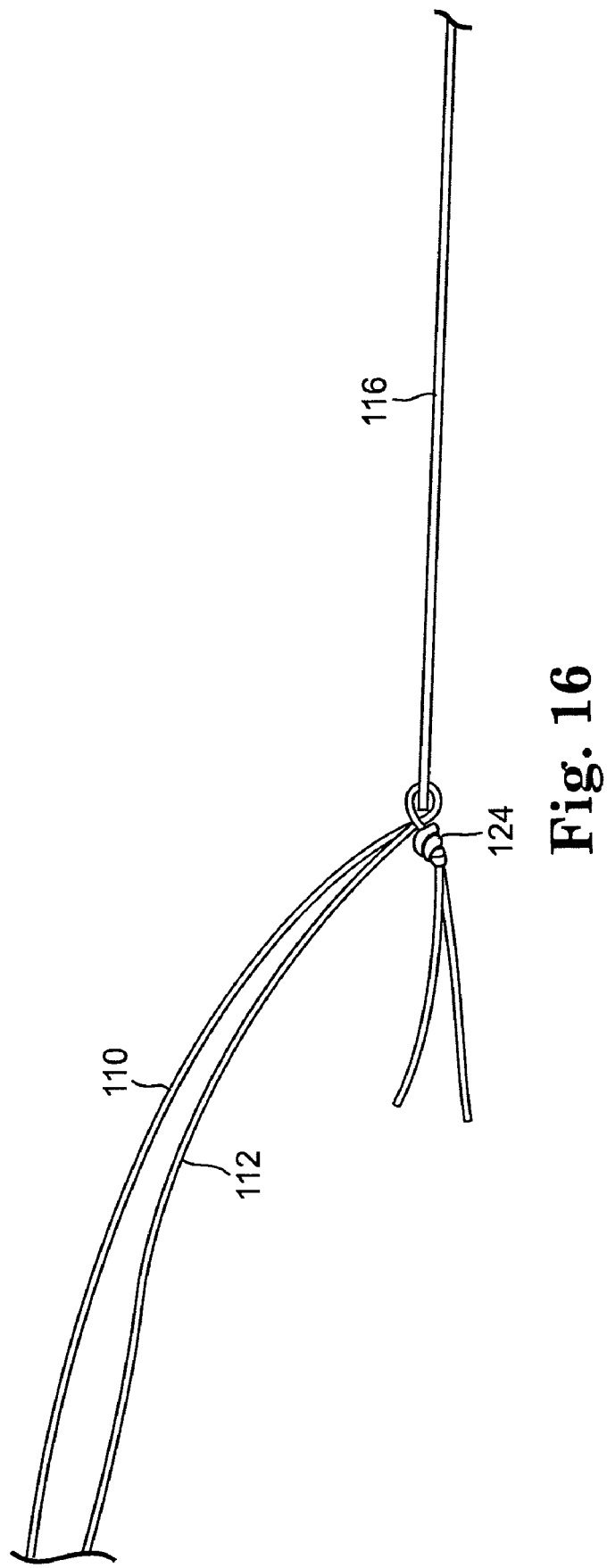
FIG. 16 is a schematic view of another step for connecting a suture to a needle with a knot in accordance with the present invention showing in particular a step of tightening the knot shown in FIG. 15 so that the knot is positioned adjacent to the needle.

One technique for connecting a needle to a suture in accordance with the present invention is illustrated in FIGS. 9-16. Referring to FIG. 9, first and second suture portions, 110 and 112, of a suture 114 are shown threaded through an eye 115 of a needle 116. Preferably, the suture 114 is also connected to a penile prosthesis (not shown), as described above, for example. Next, a loop 118 is preferably formed from the first and second suture portions, 110 and 112, as shown in FIG. 10 and the ends of the first and second suture portions, 110 and 112, are preferably passed through the loop 118 as shown in FIG. 11 to form a loose knot 120. Preferably, the ends of the first and second suture portions, 110 and 112, are passed through the loose knot 120 as shown in FIG. 12 to form the loose knot 122. Essentially, the loose knot 122 is formed by passing the suture portions, 110 and 112, through the loop 118 twice. Next, the loose knot 122 is tightened to form the knot 124 as shown in FIG. 13. As shown in FIG. 14, the needle 116 is preferably spaced from the knot 124 and the needle 116 is then preferably passed through the suture portions, 110 and 112, as illustrated in FIG. 15. The knot 124 can then be pulled against the needle 116 as shown in FIG. 16 to form the connection between the suture 114 and the needle 116.

Preferably, the material used for the suture 72 comprises sufficient strength for implanting the penile prosthesis 70 in accordance with the present invention. The material for the suture 72 is preferably capable of forming a knot having sufficient knot break strength and slipping resistance such as the knot 78 described above. Preferably, the cross-sectional area of the suture material is minimized while maintaining the desired knot break strength or slipping resistance. One exemplary material that can be used for the suture material includes ultra-high-molecular-weight-polyethylene fiber. For example, such fiber is commercially available from Teleflex Medical of Jaffrey, N.H. under the tradename of "Force Fiber." However, other materials can be used such as polyesters and/or polyblends.

If additional strength for the connection between the needle 64 and the penile prosthesis 70 is desired or if a redundant or backup connection is desired, one or more additional suture loops can be used to connect the needle 64 to the penile prosthesis 70 in accordance with the present invention. For example, in FIG. 6 the needle 64 is shown connected to the penile prosthesis 70 by the suture 72 as described above with respect to FIG. 5. The needle 64 is also connected to the penile prosthesis 70 by a second suture loop 80 of the suture 72, as shown. The suture loop 80 is threaded through the penile prosthesis 70, as shown, so that first and second suture portions 82 and 84 of the suture loop 80 extend out of the penile prosthesis 70.

Figure 8:
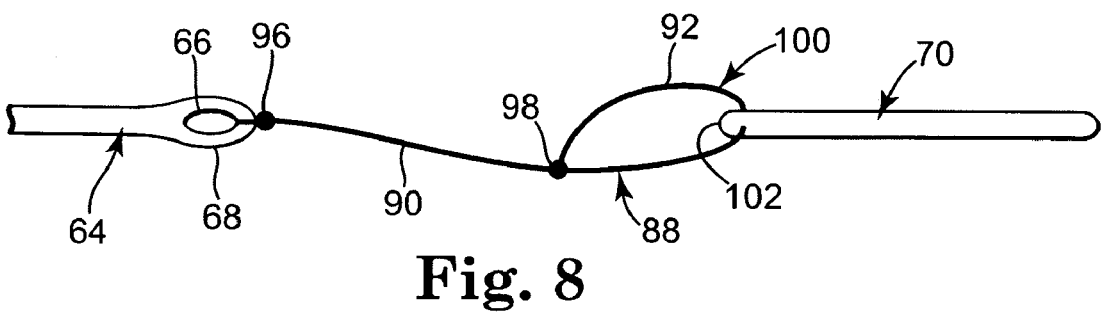
FIG. 8 is a schematic view of a penile implant device of the present invention showing in particular a suture connected to an end of a penile prosthesis and also connected to a needle with a knot wherein a suture loop is provided for removing the suture after implanting the penile implant device in accordance with the present invention.

In accordance with the present invention, a suture can be tied directly to the connecting portion 66 of the needle 68 for providing a connection to the penile prosthesis 70. For example, in FIG. 7 a suture 88 is threaded through the penile prosthesis 70 so that first and second suture portions, 90 and 92, extend out of the penile prosthesis 70, as shown. Preferably, the first and second suture portions, 90 and 92, are tied to form a knot 94 that attaches the first and second suture portions, 90 and 92, to the connecting end 68 of the needle 64. Preferably, the knot 94 is provided so that the knot 94 is behind the connecting end 68 of the needle 64 and does not slide around or move relative to the needle 64. For example, the first and second suture portions, 90 and 92, can be threaded through the eye 66 of the needle 64 and tied together to form the knot 94. Also, as shown in FIG. 8, the first suture portion 90 can be threaded through the eye 66 of the needle 64 and tied to form a knot 96, as shown. The second suture portion 92 can be tied or otherwise joined to the first suture portion 90 to form a knot 98, as shown. As such, the first and second suture portions, 90 and 92, form a loop 100 as joined by the knot 98. The knot 98 can be formed anywhere along the first suture portion 90, including a position directly adjacent to the knot 96. Preferably, the knot 98 is spaced apart from a tip portion 102 of the penile prosthesis 76 by a sufficient distance to allow the knot 98 to be positioned outside of the penis when the penile prosthesis 76 is fully implanted in the penis. As such, the loop 100 can be cut to remove the suture 88 from the penile prosthesis 76 without the need to pull the knot through glans of the penis after implantation of the penile prosthesis 76 is completed.

In use, a penile implant device according to the invention such as the penile implant device 10 described above, can be used in combination with methods of using a Keith needle and Furlow insertion device. A surgeon can remove the sheath 25 from the needle 22 (and suture 30). The penile implant device 10 can then be implanted according to known methods. In one embodiment of the present invention, a method of using such a device includes the advantage that the device includes no loose suture ends. A surgeon is able to remove the sheath 25 and hold the needle 22 (and attached suture 30) with one hand, for example, when inserting the needle into a Furlow insertion tool during surgery.

A surgeon can remove the needle 22 from the sheath 25 by holding an exposed portion of the suture 30, as well as the sheath 25, and pulling the sheath 25 away from the body portion 14. As the sheath 25 is pulled away from the body portion 14, the needle 22 is pulled from the sheath 25. The sheath 25 can be set aside. The needle 22 is then ready to be inserted into a Furlow insertion tool as if the surgeon had threaded the needle 22 in the operating room. If the needle 22 includes a protective cap or the like positioned on a sharp end of the needle 22, the protective cap may be removed from the needle 22 before loading the needle 22 into the Furlow insertion tool. Alternatively, the needle 22 may be loaded into the Furlow insertion tool while the protective cap is positioned on the needle 22. By keeping the protective cap at least partially on the needle 22 the components of the penile implant device and handlers of the needle 22 can be protected from the sharp end of the needle 22 until the needle is inserted into the Furlow tool. The needle 22 can be inserted into the Furlow tool with the protective cap in place and as the needle 22 is drawn into the Furlow tool, the protective cap can be pushed off of the end of the needle 22 by the Furlow tool. The surgeon then can use known procedures to use the Furlow insertion tool and Keith needle to position the body portion 14 of the implant device 10 within the corpus cavernosa of a patient.

The present invention is described with reference to several embodiments. The foregoing description has been given for clarity of understanding. Others may recognize that changes can be made in the described embodiments without departing from the scope and spirit of the invention. Thus, the scope of the present invention should not be limited to the exact details and structures described herein.

What is claimed is:

1. A penile implant assembly for the treatment of impotence, the penile implant assembly comprising:
    a penile prosthesis that can be implanted in a corpus cavernosa of a penis;
    a needle having a piercing end, connecting end, and a non-straight portion between piercing end and connecting end, the non-straight portion comprising at least one apex;
    a suture connected to a first end of the penile prosthesis and connected to the connecting end of the needle; and
    a removable sheath at least partially surrounding at least a portion of the needle and a first portion of the suture, wherein a second portion of the suture extends out of the removable sheath, the removable sheath comprising an interior surface in contact with the at least one apex of the non-straight portion of the needle.

2. The penile implant assembly of claim 1, wherein the interior surface of the removable sheath is in contact with at least a portion of the suture.

3. The penile implant assembly of claim 1, wherein the suture comprises polyethylene.

4. The penile implant assembly of claim 1, further including a protective cap positioned to at least partially surround the piercing end of the needle.

5. The penile implant assembly of claim 1, further comprising packaging that encloses the penile implant assembly in a sterile zone.

6. A penile implant device kit that can be provided by a manufacturer to a surgeon, the penile implant device kit comprising:
    a penile prosthesis that can be implanted in a corpus cavernosa of a penis;
    a needle having a piercing end and a connecting end;
    a suture connected to a first end of the penile prosthesis and connected to the connecting end of the needle; and
    a removable sheath surrounding at least a portion of the needle and a first portion of the suture, wherein a second portion of the suture extends out of the removable sheath.

7. The penile implant device kit of claim 6, further comprising a second penile prosthesis connected to a needle by a suture.

8. The penile implant device kit of claim 7, further comprising a fluid reservoir operatively connected to the first and second penile prostheses.

9. A method of making a penile implant assembly, the penile implant assembly comprising a penile implant device that can be implanted in a penis of a patient for the treatment of impotence, the method comprising the steps of:
    providing a penile prosthesis having an end that can be implanted in a corpus cavernosa of a penis and a needle having a piercing end and a connecting end;
    connecting a suture to the end of the penile prosthesis;
    connecting the suture to the connecting end of the needle;
    positioning at least a portion of the needle and a portion of the suture within a removable sheath so a portion of the suture extends out of the removable sheath; and
    maintaining the connection of the suture to the connecting end of the needle during at least a pre-operative storage period of the penile implant device.

10. The method of claim 9, wherein the step of connecting the suture to the end of the penile prosthesis comprises threading the suture through the end of the penile prosthesis so that first and second portions of the suture extend from the end of the penile prosthesis.

11. The method of claim 10, wherein the step of connecting the suture to the connecting end of the needle comprises threading at least one of the first and second suture portions through an eye at the connecting end of the needle.

12. The method of claim 11, wherein the step of connecting the suture to the connecting end of the needle comprises tying the first and second suture portions together to form a knot.

13. The method of claim 9, wherein the step of positioning at least a portion of the needle inside a sheath comprises resistively engaging at least a portion of an inside surface of the sheath with at least a portion of the needle after connecting the suture to the connecting end of the needle.

14. The method of claim 9, further comprising the step of packaging the penile prosthesis connected to the needle for storage during a pre-operative storage period of the penile implant device.

15. A method of implanting a penile prosthesis of a penile implant assembly in a penis of a patient for the treatment of impotence, the method comprising the steps of:

providing a penile implant assembly comprising a penile prosthesis that has been connected to a needle by a suture during a pre-operative storage period of the penile implant device, wherein at least a portion of the needle and a portion of the suture are positioned within a removable sheath;

removing the sheath from the penile implant device;

positioning the needle and at least a portion of the suture in a corpus cavernosa of a penis, piercing the glans of the penis with the needle, and drawing at least a portion of the suture through the glans of the penis with the needle; and positioning the penile prosthesis in the corpus cavernosa of the penis.

16. The method of claim 15, wherein the step of providing a penile implant assembly comprises removing the penile implant device from a package that the penile implant device has been stored in during the pre-operative storage period of the penile implant device.

* * * * *